United States Patent [19]
Meerpohl et al.

[11] Patent Number: 6,067,845
[45] Date of Patent: May 30, 2000

[54] METHOD OF DETERMINING A MOISTURE CONTENT OF TEXTILE GOODS IN A LAUNDRY DRIER

[75] Inventors: Hansjörg Meerpohl; Dietmar Pech, both of Berlin, Germany

[73] Assignee: BSH Bosch und Siemens Hausgeraete GmbH, Munich, Germany

[21] Appl. No.: 09/268,268

[22] Filed: Mar. 15, 1999

[30] Foreign Application Priority Data

Mar. 13, 1998 [DE] Germany .............................. 198 11 021

[51] Int. Cl.$^7$ .............................. G01N 5/02; F26B 13/10
[52] U.S. Cl. .................................. 73/73; 34/524; 34/528; 34/532
[58] Field of Search .................................. 73/73; 34/524, 34/528, 532, 533, 550

[56] References Cited

U.S. PATENT DOCUMENTS

| | | | |
|---|---|---|---|
| 3,758,959 | 9/1973 | Karklys | 34/533 |
| 3,818,603 | 6/1974 | Marcade | 34/532 |
| 5,737,852 | 4/1998 | Shukla et al. | 34/528 |

*Primary Examiner*—William Oen
*Attorney, Agent, or Firm*—Herbert L. Lerner; Laurence A. Greenberg; Werner H. Stemer

[57] ABSTRACT

The electrical conductivity of laundry in a laundry drum is measured and the moisture content is determined from the measured quantity. A polarization voltage, which corrupts the measurement result, is formed at the electrodes. In order to compensate for this disturbing influence, as well as for other material and aging effects, the conductivity measurement is briefly interrupted and the polarization voltage which is present across the electrodes and has formed during the conductivity measurement is measured. The measured error voltage is used to compensate the laundry voltage measured during the previous conductivity measurement. This improves the determination of the conductivity, and thus of the moisture content, considerably. The method is particularly suitable for a microcontroller.

15 Claims, 1 Drawing Sheet

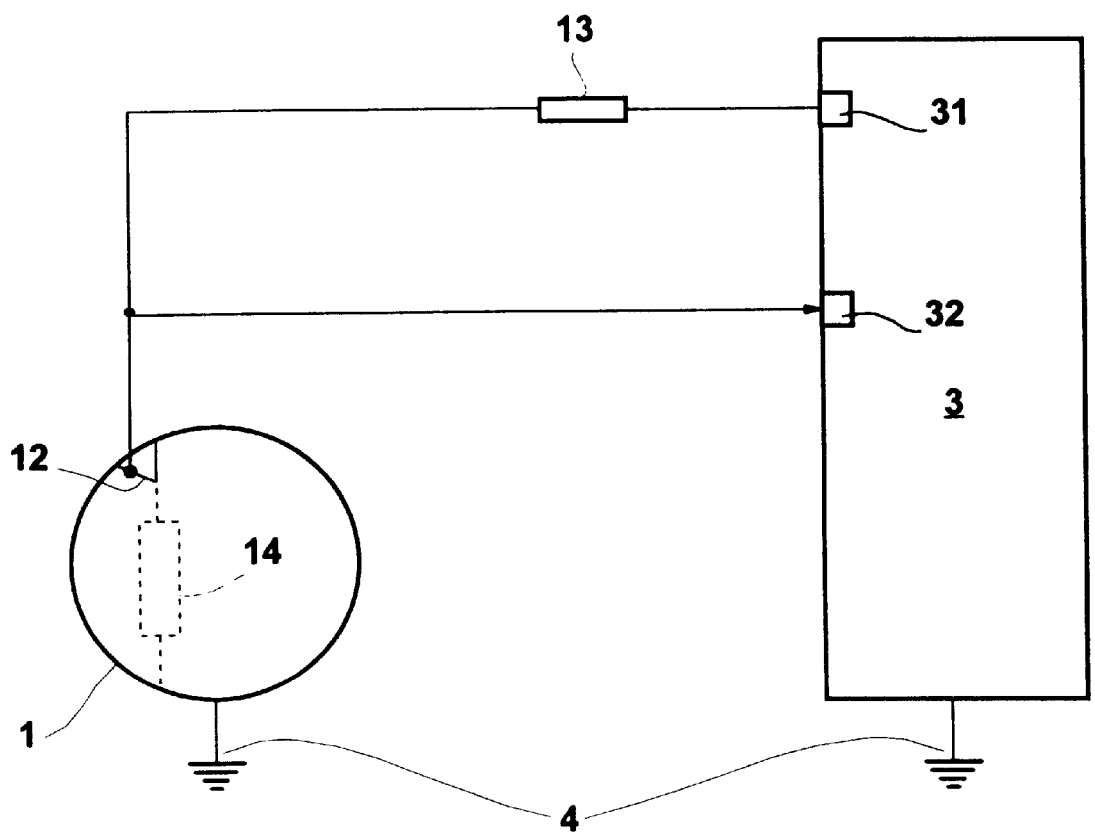

METHOD OF DETERMINING A MOISTURE CONTENT OF TEXTILE GOODS IN A LAUNDRY DRIER

BACKGROUND OF THE INVENTION

FIELD OF THE INVENTION

The present invention relates to a method for determining the moisture content of textile goods in a laundry drier. In general, electric current is passed through the textile goods via electrodes which touch the textile goods and the laundry voltage drop across the textile goods is determined at the electrodes. The conductivity of the textile goods is determined from the laundry voltage. The moisture content of the textile goods is then determined from the conductivity.

When drying textile goods in a laundry drier, it is a major advantage to know the actual moisture content of the textile goods. This information can be used, for example, to determine the remaining time for the drying process, to control the drying process optimally, or to match the heating power to the requirement. Furthermore, if the moisture content is known, the drying process can be ended exactly at the desired residual moisture content. The optimum residual moisture content can be set irrespective of what else is to be done to the textile goods. If, for example, it is intended to iron the textile goods after drying, a higher residual moisture content is advantageous than for storing them.

The moisture content of textile goods in a laundry drier is normally determined by measuring their electrical conductivity. The moisture content is thereby proportional to the conductivity. As a rule, two electrodes are applied to the textile goods for this purpose, one of which is normally the drum in which the textile goods are located. A voltage is applied via a resistor to the two electrodes, and causes current to flow through the textile goods. The laundry voltage drop across the textile goods is measured at the electrodes. The voltage drop is used to determine the conductivity, and the moisture content, of the textile goods.

A disadvantageous feature of this method is that, when a voltage for conductivity measurement is applied between the moist textile goods and the electrodes, a battery element is formed, whose voltage is dependent in particular on the conductivity of the water, the nature and composition of the materials used, and the magnitude and polarity of the voltage applied for measurement. This battery element voltage, which is called the "polarization voltage" in the following text, can be superimposed on the laundry voltage drop across the textile goods, and can thus corrupt the determination of the conductivity. The polarization voltage occurs, in particular, with moist laundry, so that wetter laundry items are more severely affected by it.

German published patent application DE 34 17 482 A1 discloses a method in which the conductivity of the textile goods is measured when they are still wet at the start of the drying process. There is thus also determined, inter alia, a correction factor which is dependent on the laundry drier load and on the conductivity of the water. The correction factor is stored and is used during the drying process to correct the measured conductivity, which is corrupted by various factors. The polarization voltage is thereby also detected and is compensated for. It is disadvantageous that the correction value is determined only at the start of the drying process, so that changes in the polarization voltage during drying cannot be taken into account. Furthermore, the correction value is dependent on a number of influencing variables, which are subject to different changes, so that objective compensation for the polarization voltage is impossible.

Methods are also known from the prior art in which a pulsed d.c. voltage or an a.c. voltage is used to measure the conductivity of the textile goods. The resulting polarization voltage is very low or does not occur at all. These methods have, in particular, the disadvantage that they involve a high level of complexity to produce the specific measurement voltage and to determine the conductivity and the moisture content.

SUMMARY OF THE INVENTION

It is accordingly an object of the invention to provide a method for determining the moisture content of textile goods in a laundry drier, which overcomes the above-mentioned disadvantages of the heretofore-known devices and methods of this general type and which compensates for the above-described corruption of the conductivity determination by the polarization voltage.

With the foregoing and other objects in view there is provided, in accordance with the invention, a method of determining a moisture content of textile goods in a laundry drier, which comprises:

contacting textile goods with electrodes and passing electric current through the textile goods;

temporarily interrupting, or greatly reducing, the electric current through the textile goods and determining a polarization voltage between the electrodes and the textile goods at the electrodes touching the textile goods;

determining a laundry voltage drop across the textile goods at the electrodes and deriving a conductivity of the textile goods from the laundry voltage and taking into account the polarization voltage; and defining a moisture content of the textile goods from the conductivity of the textile goods.

In other words, the determination of the conductivity is interrupted, and the current flow through the textile goods is temporarily interrupted, or is at least greatly reduced. The polarization voltage between the electrodes and the textile goods can then be determined at the electrodes which touch the textile goods. This polarization voltage is taken into account in the determination of the electrical conductivity of the textile goods.

When the current flow through the textile goods is switched off, there is no longer any laundry voltage drop across them, so that the voltage measured across the electrodes in this case corresponds essentially to the polarization voltage. This means that the polarization voltage can thus be determined and can be taken into account in the conductivity determination. The novel method allows the disturbance influence of the polarization voltage to be determined, and to be compensated for in the determination of the conductivity, with the circuit complexity remaining the same, or being only slightly increased. Furthermore, this method allows the electrochemical influences resulting from material differences to be eliminated. In addition, aging effects in the materials and the different conductivity of the water contained in the textile goods can be taken into account and compensated for continuously.

In accordance with an added feature of the invention, the polarization voltage or a correction value that takes the polarization voltage into account is subtracted from the laundry voltage.

For example, the polarization voltage can be taken into account by subtracting it, or a correction value that takes it into account, from the laundry voltage. In the simplest case, the polarization voltage can be directly subtracted from the laundry voltage, so that the latter is compensated just by this simple computation operation. However, in practice it may be necessary to determine a correction value based on the polarization voltage, which is subtracted from the laundry voltage. This is advantageous in those cases in which the measured polarization voltage does not match that which acts during the conductivity measurement, and corrupts it.

A delay time is advantageously allowed to pass between the determination of the conductivity and the determination of the polarization voltage, during which delay time the current flow through the textile goods is interrupted, or is at least greatly reduced. This time allows the polarization voltage to reach a steady state, so that it can be determined more reliably. Any change in the value which may occur in this time can be taken into account, as described above, by forming a correction value.

From experience, a delay time of about at least three to ten seconds, and preferably of at least five seconds, is sufficient. This allows an advantageous compromise to be reached between a reliable and fast determination of the polarization voltage.

The current flow through the textile goods is produced in a simple manner by a voltage which is connected via a resistor to the electrodes which touch the textile goods. Since, virtually without exception, laundry driers are electrically powered and, in consequence, have various voltages available anyway, a current flow through the textile goods can be produced in this way with very little circuit complexity.

In order to interrupt or to reduce the current flow through the textile goods, the voltage is switched off or is reduced. The circuits used in the electrical system or electronics normally have voltage outputs with different voltages, which can be switched on or off as required. Moreover, so-called "three-state outputs" also exist, which can also be switched to a high-impedance state in which there is no defined voltage at the output, and no current can flow. The current flow can thus be interrupted or reduced by means of conventional components, by varying or switching off the output voltage.

The current flow can also be interrupted or reduced by increasing the resistance connected in series with the electrodes or by reducing the current flowing through this resistance. A variable resistor can be used for this purpose, for example a photoresistor or an optocoupler, by means of which the current can be varied. A controllable switching element can also be connected in series with a non-variable resistor, and is switched off in order to interrupt the current flow. This allows any desired voltage source to be used, in particular even a source with a relatively high or particularly constant voltage, without having to switch off or vary the voltage source itself.

A microprocessor or a microcontroller is advantageously used to produce and/or to determine electrical voltages and/or to determine the delay time, to which microprocessor or microcontroller an analog/digital converter may possibly be assigned, for voltage measurement.

This is particularly advantageous when a microprocessor or microcontroller is used to control the laundry drier anyway since, in such a case, no additional component or circuitry complexity is required. Since, as a rule, the way in which a microprocessor or microcontroller operates depends on its programming, a suitable selection of memory devices for the program code provides the capability to vary the programming retrospectively, in order to implement additional methods or to vary those already implemented.

In one particularly advantageous embodiment, the method according to the invention is carried out by a microprocessor or a microcontroller. If required, devices for voltage measurement may be assigned to the microprocessor or microcontroller.

It is particularly worthwhile using a microcontroller when one is used anyway to control the laundry drier. The method according to the invention can be implemented without any additional complexity in such a case, and can be carried out accurately and reliably by means of the microcontroller.

Other features which are considered as characteristic for the invention are set forth in the appended claims.

Although the invention is illustrated and described herein as embodied in a method for determining the moisture content of textile goods in a laundry drier, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE DRAWINGS

The figure is a schematic diagram of a circuit for carrying out the method according to the invention.

DESCRIPTION OF THE PREFERRED EMBODIMENTS

Referring now to the sole figure of the drawing in detail, there is seen a schematic system representing the process of the invention. A resistor 14 in a drum 1 represents the textile goods to be dried as an electrical equivalent. The resistor 14 is disposed (connected) between a first electrode—the laundry drum 1—and a second electrode 12. The second electrode 12 is an element that is mounted so as to electrically insulated from the drum. The drum 1 is connected to the appliance ground 4. The electrode 12 is connected on the one hand to an analog/digital input 32 of a microcontroller 3, and on the other hand via a resistor 13 to a digital output 31 of the microcontroller 3. The microcontroller 3 is likewise connected to the appliance ground 4.

In order to determine the moisture content of the textile goods, the voltage output 31 is switched on, as a result of which a current flows via the resistor 13 and through the laundry resistance 14, resulting in a voltage drop across the latter. The laundry voltage, which is dropped across the laundry between the electrodes 1 and 12, is applied to the analog/digital input 32, and is measured by the latter.

Once this measurement has been completed, the voltage output 31 is switched off, so that no more current flows through the resistance 14 of the textile goods, and no voltage drop is produced across it, either. In this stage, essentially all that acts is the polarization voltage which has been formed by the previous current flow and exists between the textile goods and the electrodes 1 and 12. After a delay time of five seconds has passed, which is determined by the microcontroller 3, the polarization voltage is measured at the electrode 12, via the analog/digital input 32.

In a further step, the polarization voltage is subtracted, in the arithmetic unit of the microcontroller 3, from the laundry voltage measured in the preceding step. The difference voltage corresponds to the corrected laundry voltage from which, for example by forming the reciprocal, the conductivity and thus the moisture content of the textile goods can be determined.

The solution according to the invention thus provides a method for determining the moisture content of textile goods in a laundry drier, in which method the polarization voltage in the conductivity measurement can be compensated for, and the determination of the moisture content can be improved, with no additional complexity, or with only very little additional complexity.

This compensation method also allows aging and material effects to be taken into account as well. The method can be used particularly advantageously in laundry driers in which there is a microcontroller anyway, and used to measure the conductivity of the textile goods.

However, the invention is not limited to the described embodiment. For example, it is also conceivable to use electrodes other than those that are used for the conductivity measurement to measure the polarization voltage, which may be formed even without a current flow, and to use this voltage, measured in parallel with the conductivity, to correct the conductivity measurement. The parallel measurement of the polarization voltage can also be carried out after current has previously flowed through the electrodes, in order to produce a polarization voltage which corresponds to that which occurs during the conductivity measurement.

We claim:

1. A method of determining a moisture content of textile goods in a laundry drier, which comprises:

contacting textile goods with electrodes and passing electric current through the textile goods;

temporarily reducing the electric current through the textile goods and determining a polarization voltage between the electrodes and the textile goods at the electrodes touching the textile goods;

determining a laundry voltage drop across the textile goods at the electrodes and deriving a conductivity of the textile goods from the laundry voltage and taking into account the polarization voltage; and defining a moisture content of the textile goods from the conductivity of the textile goods.

2. The method according to claim 1, wherein the temporarily reducing step comprises interrupting the current flow through the textile goods.

3. The method according to claim 1, which comprises subtracting one of the polarization voltage or a correction value taking into account the polarization voltage from the laundry voltage.

4. The method according to claim 1, which comprises inserting a delay time between the step of deriving the conductivity and the step of determining the polarization voltage, and reducing the current flow through the textile goods during the delay time.

5. The method according to claim 4, wherein the reducing step comprises interrupting the current flow through the textile goods during the delay time.

6. The method according to claim 4, which comprises defining the delay time to between 3 seconds and 10 seconds.

7. The method according to claim 4, which comprises defining the delay time to substantially 5 seconds.

8. The method according to claim 1, wherein the step of passing current through the textile goods comprises connecting a voltage to the electrodes touching the textile goods via a resistor.

9. The method according to claim 8, wherein the reducing step comprises reducing the voltage supply to the electrodes.

10. The method according to claim 9, wherein the reducing step comprises increasing a resistance of the resistor.

11. The method according to claim 8, wherein the reducing step comprises completely interrupting the voltage supply to the electrodes.

12. The method according to claim 11, wherein the interrupting step comprises increasing a resistance of the resistor.

13. The method according to claim 1, which comprises carrying out at least one step selected from the group consisting of producing an electrical voltage, determining the voltage drop, defining a delay time, and defining the moisture content of the textile goods with a microprocessor.

14. The method according to claim 1, which comprises performing the steps with a microprocessor.

15. The method according to claim 1, which comprises performing the steps with a microcontroller.

* * * * *